United States Patent
Yoo et al.

(10) Patent No.: US 10,957,419 B2
(45) Date of Patent: Mar. 23, 2021

(54) METHOD AND APPARATUS FOR NEW MATERIAL DISCOVERY USING MACHINE LEARNING ON TARGETED PHYSICAL PROPERTY

(71) Applicant: SAMSUNG ELECTRONICS CO., LTD., Suwon-si (KR)

(72) Inventors: Jiho Yoo, Hwaseong-si (KR); Seokho Kang, Seoul (KR); Youngchun Kwon, Yongin-si (KR); Kyung doc Kim, Seoul (KR); Jaikwang Shin, Seoul (KR); Hyosug Lee, Suwon-si (KR); Younsuk Choi, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 859 days.

(21) Appl. No.: 15/664,960

(22) Filed: Jul. 31, 2017

(65) Prior Publication Data
US 2018/0032663 A1    Feb. 1, 2018

(30) Foreign Application Priority Data
Aug. 1, 2016    (KR) ........................ 10-2016-0097764

(51) Int. Cl.
*G16B 15/00*    (2019.01)
*G06N 20/00*    (2019.01)
(Continued)

(52) U.S. Cl.
CPC .............. *G16B 15/00* (2019.02); *G06N 5/04* (2013.01); *G06N 20/00* (2019.01); *G16B 40/00* (2019.02); *G06N 3/0445* (2013.01)

(58) Field of Classification Search
None
See application file for complete search history.

(56) References Cited

U.S. PATENT DOCUMENTS

| | | | |
|---|---|---|---|
| 4,939,666 A | 7/1990 | Hardman | |
| 5,463,564 A | 10/1995 | Agrafiotis et al. | |

(Continued)

FOREIGN PATENT DOCUMENTS

| | | | |
|---|---|---|---|
| JP | H10505832 A | 6/1998 | |
| JP | 2002501233 A | 1/2002 | |

(Continued)

OTHER PUBLICATIONS

Isayeve et al., Materials Cartography: Representing and Mining Materials Space Using Structural and Electronic Fingerprints, Chem. Mater. 2015, 27, pp. 735-743 (Year: 2015).*

(Continued)

*Primary Examiner* — Alan Chen
(74) *Attorney, Agent, or Firm* — Cantor Colburn LLP (57) ABSTRACT

A structure-generating method for generating a structure candidate of a new material including: by a structure-generating processor: performing machine learning on a machine learning model, wherein the machine learning model is configured to provide a result based on a descriptor of a material, a physical property of the material, and a structure of the material; and generating a structure candidate of the new material based on the result of the machine learning, wherein the new material has a target physical property, and wherein the descriptor of the material, the physical property of the material, and the structure of the material are stored in a database.

24 Claims, 9 Drawing Sheets

(51) Int. Cl.
G16B 40/00 (2019.01)
G06N 5/04 (2006.01)
G06N 3/04 (2006.01)

(56) References Cited

U.S. PATENT DOCUMENTS

| | | | |
|---|---|---|---|
| 5,574,656 A | 11/1996 | Agrafiotis et al. | |
| 5,684,711 A | 11/1997 | Agrafiotis et al. | |
| 5,901,069 A | 5/1999 | Agrafiotis et al. | |
| 6,434,490 B1 | 8/2002 | Agrafiotis et al. | |
| 8,849,575 B2 * | 9/2014 | Gustafsson | G16B 20/00 |
| | | | 702/19 |
| 2003/0033088 A1 | 2/2003 | Agrafiotis et al. | |
| 2005/0240355 A1 * | 10/2005 | Brown | G16C 20/50 |
| | | | 702/19 |
| 2017/0124482 A1 * | 5/2017 | Yoo | G06F 16/245 |

FOREIGN PATENT DOCUMENTS

| | | |
|---|---|---|
| JP | 2003058579 A | 2/2003 |
| JP | 2006323833 A | 11/2006 |
| JP | 2010198561 A | 9/2010 |
| KR | 1020040050372 A | 6/2004 |
| KR | 1020120085148 A | 7/2012 |

OTHER PUBLICATIONS

Ghiringhelli et al., Big Data of Materials Science: Critical Role of the Descriptor, Physical Review Letters, 114, 105503, 2015, Total pp. 5 (Year: 2015).*

Sukumar et al., Molecular Descriptors for Biological Systems, Rensselaer Exploratory Center for Cheminformatics Research, Total pp. 46 (Year: 2011).*

Breiman, Random Forests, Machine Learning, 45, 2001, pp. 5-32 (Year: 2001).*

Xue et al., Accelerated search for materials with targeted properties by adaptive design, Nature Communications, 7:11241, pp. 1-0 (Year: 2016).*

Barbara Hammer, "Recurrent networks for structured data—a unifying approach and its properties", Cognitive Systems Research, vol. 3, No. 2, 2002, pp. 145-465.

Cerqueira et al., "Materials Design On-the-Fly", JCTC, 11, 2015, 3955-3960.

Frasconi et al., "A General Framework for Adaptive Processing of Data Structures", IEEE Transactions on Neural Networks, vol. 9, No. 5, Sep. 1998, 768-786.

Jain et al., "A High-throughput infrastructure for density functional theory calculations", Computational Materials Science, 50, 2011, 2295-2310.

Miyao et al., "Inverse QSPR/QSAR Analysis for Chemical Structure Generation (from y to x)", Journal of Chemical Information and Modeling, vol. 56, No. 2, 2016, pp. 286-299.

Miyao et al., "Exhaustive Structure Generation for Inverse-QSPR/QSAR", Molecular Informatics, 29, 2010, 111-125.

Pilania et al., "Accelerating materials property predictions using machine learning", Sci. Rep., 3, 2013, 1-6.

Salakhutdinov et al., "Deep Boltzmann Machines", 12th International Conference on Artificial Intelligence and Statistics, 2009, 1-8.

White et al., "Generative Models for Chemical Structures", J. Chem. Inf. Model., 50, 2010, 1257-1274.

Wong et al., "A constructive approach for discovering new drug leads: Using a kernel methodology for the inverse-QSAR problem", Journal of Cheminformatics, 2009, p. 1-27.

* cited by examiner

<STRUCTURAL FORMULA>                <DESCRIPTOR>

METHOD AND APPARATUS FOR NEW MATERIAL DISCOVERY USING MACHINE LEARNING ON TARGETED PHYSICAL PROPERTY

CROSS-REFERENCE TO RELATED APPLICATION

This application claims priority to and the benefit of Korean Patent Application No. 10-2016-0097764, filed in the Korean Intellectual Property Office on Aug. 1, 2016, and all the benefits accruing therefrom under 35 U.S.C. § 119, the content of which in its entirety is herein incorporated by reference.

BACKGROUND

(1) Field of the Invention

This disclosure relates to a method and an apparatus for generating a structure candidate of a new material.

(2) Description of the Related Art

First principles calculation techniques can be used to predict the characteristics of a material without using direct measurements and related experiments. Further, as high-performance computing techniques based on supercomputers are developed, the evaluation of an array of material candidates can be performed using a high-throughput computational screening method that is faster and more efficient than the direct synthesis and characterization of the array of material candidates using conventional methods.

A screening search range is determined for the high-throughput computational screening method. The screening search range may be selected by a researcher depending on conditions of determining a material in a specific database, or may be determined to generate a new material by modifying or combining existing materials by a rule. Success or failure of the high-throughput computational screening depends on how well the search range is determined, but the screening search range is generally determined based on experience and intuition of a researcher.

Material development techniques seek to develop a material that significantly exceeds the performance of existing materials, and thus it is oftentimes required to repeatedly perform search range setting and computational screening multiple times to obtain target performance. Typically, when a new target material candidate is not found in a determined search range, an idea for setting a new search range is drawn by analyzing an existing screening result, and the new search range is determined based on the drawn idea. However, in this case, it is difficult to directly analyze and determine a next search region due to a large amount of calculation data.

SUMMARY

An embodiment provides a method for generating a structure candidate of a new material that has a target physical property depending on a result of machine learning that is performed based on a descriptor, a physical property, and a structure of an existing material.

An embodiment provides an apparatus for generating a structure candidate of a new material that has a target physical property depending on a result of machine learning that is performed based on a descriptor, a physical property, and a structure of an existing material.

An embodiment provides a structure-generating method for generating a structure candidate of a new material. The structure-generating method may include, by a structure-generating processor, performing machine learning on a machine learning model. The machine learning model is configured to provide a result based on a descriptor of a material, a physical property of the material, and a structure of the material. The structure-generating method may further include, by the structure-generating processor, generating a structure candidate of the new material. The new material has a target physical property, and the descriptor of the material, the physical property of the material, and the structure of the material are stored in a database.

The performing of the machine learning on the machine learning model configured to provide a result based on the descriptor of the material, the physical property of the material, and the structure of the material may include, by the structure-generating processor: determining a factor indicating a relationship between the descriptor and the structure by performing the machine learning on a relationship between the descriptor and the physical property; and performing the machine learning on a relationship between the factor and the structure, and generating the structure of the material based on a result of the machine learning on the relationship between the factor and the structure The performing of the machine learning on the relationship between the factor and the structure may include, by the structure-generating processor, determining a structural factor indicating the relationship between the factor and structure.

The factor may include a plurality of layers, and the determining of the structural factor may include, by the structure-generating processor, determining the structural factor for each layer of the plurality of layers.

The determining of the factor may include, by the structure-generating processor: learning an encoding function for deriving the factor from the descriptor based on data related to each of the descriptor and the physical property; and determining the factor by applying the encoding function to the descriptor.

The performing of the machine learning on the relationship between the factor and the structure further includes, by the structure-generating processor, learning a decoding function for generating the structure candidate from the factor based on data relating to each of the factor and the structure.

The generating of the structure candidate may include, by the structure-generating processor: sampling a factor corresponding to the target physical property; and generating the structure candidate by applying the decoding function to the factor corresponding to the target physical property.

The performing of the machine learning on the machine learning model configured to provide a result based on the descriptor of the material, the physical property of the material, and the structure of the material may further include, by the structure-generating processor, learning a prediction function for predicting the physical property from the factor based on data relating to each of the descriptor and the physical property.

The generating of the structure candidate further includes, by the structure-generating processor: generating an arbitrary descriptor; predicting a physical property of a material corresponding to the arbitrary descriptor by applying the prediction function to the arbitrary descriptor; and determining whether the predicted physical property of the material corresponding to the arbitrary descriptor has the target physical property.

The generating of the structure candidate may further include, by structure-generating processor, when the predicted physical property of the material corresponding to the arbitrary descriptor does not have the target physical property: generating an arbitrary descriptor different from the arbitrary descriptor; predicting a physical property of a material corresponding to the different arbitrary descriptor by applying the prediction function to the different arbitrary descriptor; and determining whether the predicted physical property of the material corresponding to the different arbitrary descriptor has the target physical property.

The generating of the structure candidate may further include, by the structure-generating processor, when the predicted physical property of the material corresponding to the arbitrary descriptor has the target physical property: determining a factor corresponding to the arbitrary descriptor by applying an encoding function for deriving the factor corresponding to the arbitrary descriptor; and generating a structure candidate corresponding to the arbitrary descriptor by applying a decoding function for generating the structure candidate from the factor corresponding to the arbitrary descriptor.

The structure-generating method may further include, by the structure-generating processor, performing a validity check and a redundancy check on the structure candidate corresponding to the arbitrary descriptor.

An embodiment provides a structure-generating apparatus for generating a structure candidate of a new material. The structure-generating apparatus may include a database configured to store a descriptor of a material, a physical property of the material, and a structure of the material; and a structure-generating processor configured to: perform machine learning on a machine learning model, wherein the machine learning model is configured based on the descriptor, the physical property, and the structure, and generate a structure candidate of the new material based on a result of the machine learning, wherein the new material has a target physical property.

When performing the machine learning on the machine learning model configured to provide a result based on the descriptor of the material, the physical property of the material, and the structure of the material, the structure-generating processor is configured to: determine a factor indicating a relationship between the descriptor and the structure by performing the machine learning on a relationship between the descriptor and the physical property, and perform the machine learning on a relationship between the factor and the structure to generate the structure of the material based on the factor.

When performing the machine learning on the relationship between the factor and the structure, the structure-generating processor is further configured to determine a structural factor indicating the relationship between the factor and the structure.

The factor may include a plurality of layers, and, when determining the structural factor, the structure-generating processor is further configured to determine the structural factor for each layer of the plurality of layers.

When determining the factor, the structure-generating processor is further configured to learn an encoding function for deriving the factor from the descriptor based on data related to each of the descriptor and the physical property, and to determine the factor by applying the encoding function to the descriptor.

When performing the machine learning on the relationship between the factor and the structure, the structure-generating-processor is further configured to learn a decoding function for generating the structure candidate from the factor based on data relating to each of the factor and the structure.

When generating the structure candidate, the structure-generating processor is further configured to sample a factor corresponding to the target physical property, and generate the structure candidate by applying the decoding function to the factor corresponding to the target physical property.

When performing the machine learning on the machine learning model configured to provide a result based on the descriptor of the material, the physical property of the material, and the structure of the material, the structure-generating processor is further configured to learn a prediction function for predicting the physical property from the factor based on data relating to each of the descriptor and the physical property.

When generating the structure candidate, the structure-generating processor is further configured to generate an arbitrary descriptor, predict a physical property of a material corresponding to the arbitrary descriptor by applying the prediction function to the arbitrary descriptor, and determine whether the predicted physical property of the material corresponding to the arbitrary descriptor has the target physical property.

When generating the structure candidate, when the predicted physical property of the material corresponding to the arbitrary descriptor does not have the target physical property, the structure-generating processor is further configured to generate an arbitrary descriptor different from the arbitrary descriptor, predict a physical property of a material corresponding to the different arbitrary descriptor by applying the prediction function to the different arbitrary descriptor, and determine whether the predicted physical property of the material corresponding to the different arbitrary descriptor has the target physical property.

When generating the structure candidate, when the predicted physical property of the material corresponding to the arbitrary descriptor has the target physical property, the structure-generating processor is further configured to determine a factor corresponding to the arbitrary descriptor by applying an encoding function for deriving the factor to the arbitrary descriptor, and generate a structure candidate corresponding to the arbitrary descriptor by applying a decoding function for generating the structure candidate from the factor corresponding to the arbitrary descriptor.

The structure-generating processor is further configured to perform a validity check and a redundancy check on the structure candidate corresponding to the arbitrary descriptor.

According to an embodiment of the present disclosure, it is possible to develop a new material having improved performance for use in various fields such as semiconductors, displays, batteries, catalysts, and diagnostic devices by generating a structure of the new material that is expected to have a target physical property through machine learning based on data.

BRIEF DESCRIPTION OF THE DRAWINGS

The above and other advantages and features of this disclosure will become more apparent by describing in further detail exemplary embodiments thereof with reference to the accompanying drawings, in which.

DETAILED DESCRIPTION

In the following detailed description, embodiments of the present disclosure have been shown and described, by way of illustration. As those skilled in the art would realize, the described embodiments may be modified in various different ways, all without departing from the spirit or scope of the present disclosure. Accordingly, the drawings and description are to be regarded as illustrative in nature and not restrictive, and like reference numerals designate like elements throughout the specification.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Material development technologies seek to develop materials that significantly exceed the performance of existing materials, and thus it is oftentimes required to repeatedly perform search range setting and computational screening to obtain target performance. When a new target material candidate is not found within a determined search range, an idea for setting a new search range is drawn by analyzing an existing screening result, and the new search range is determined based on the drawn idea. However, in this case, it can be difficult to directly analyze and determine a next search region due to a large amount of calculation data. Exemplary embodiments described herein provide improvements to the technological field of material development that are capable of intelligently searching, screening, and adjusting parameters to obtain a material having a desired target performance.

Figure 1:
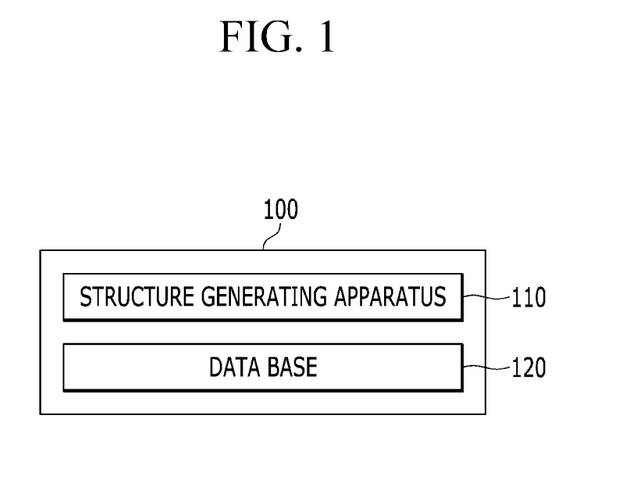
FIG. 1 is a block diagram illustrating an exemplary embodiment of a structure-generating apparatus.

FIG. 1 is a block diagram illustrating an exemplary embodiment of a structure-generating apparatus of a new material.

Referring to FIG. 1, the structure-generating apparatus 100 of the new material includes a structure-generating processor 110 and a database 120.

The structure-generating processor 110 serves to perform machine learning on a machine learning model, wherein the machine learning model is configured to provide a result based on a descriptor of a material, a physical property of the material, and a structure of the material. The structure-generating processor 110 also models relationships between the descriptor of the material, the physical property of the material, and the structure of the material, and generates a structure candidate of a new material. The structure-generating processor 110 may include a machine learning unit and a decoder (not shown).

In the database 120, a descriptor of the material, the physical property of the material, and the structure of the material are stored as one set. The structure-generating processor 110 may perform the machine learning on a machine learning model based on the descriptor of the material, the physical property of the material, and the structure of the material, which are stored in the database 120. For example, several thousands to several tens of thousands or more sets of the descriptor of the material, the physical property of the material, and the structure of the material may be stored in the database 120. The descriptor of the material and the physical property of the material may be extracted from the structure of the material by a physical property extracting device (not illustrated).

Figure 2:
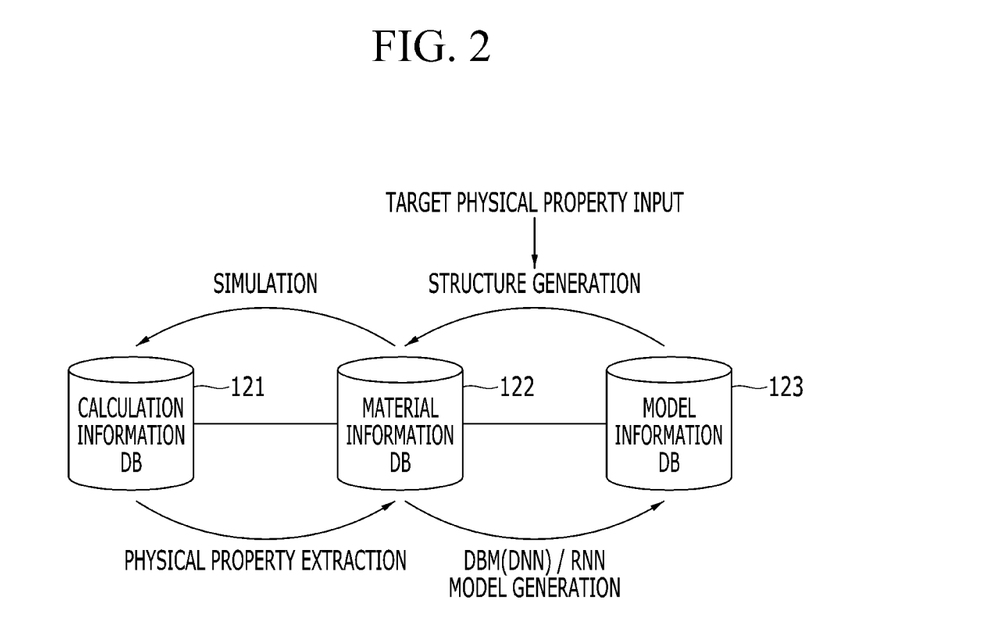
FIG. 2 is a schematic view illustrating an exemplary embodiment of a database of a structure-generating apparatus and a workflow of a structure-generating method.

FIG. 2 is a schematic view illustrating an exemplary embodiment of a database of a structure-generating apparatus and a workflow of a structure-generating method.

Referring to FIG. 2, the database 120 according to an embodiment includes a calculation information database 121, a material information database 122, and a model information database 123.

In the calculation information database 121, a result is simulated by the structure-generating processor 110 based on information stored in the material information database 122. In this case, the simulated result may be a quantum-computed result. Options used in the quantum computation, calculation progress, calculation output results, and the like, as well as the simulated result(s) may be stored in the calculation information database 121. The physical property extracting device may extract the physical property of the material from the structure of the material based on the simulated result(s) stored in the calculation information database 121.

In the material information database 122, information related to a descriptor, a structure (e.g., a structural formula, a SMILES (Simplified Molecular-Input Line-Entry System) character string, or the like), and a physical property of each material are grouped and stored. In the case of a newly generated structure candidate, information related to the physical property thereof is not yet stored in the material information database 122. The information related to the physical property of the structure candidate may be extracted from the structure of the material based on the simulated result stored in the calculation information database 121, and then may be stored in the material information database 122. Descriptor-physical property-structure data stored in the material information database 122 is used as learning data for forming a machine learning model.

In the model information database 123 stores information related to the machine learning model that is formed based on the learning data stored in the material information database 122. The information related to the machine learning model includes information related to a version of the model, a structure of the model, and a parameter of the model. Information related to the structure of the model includes the number of layers of a neural network included in the machine learning model or the number of nodes of each of the layers. The parameter of the model indicates a weighted value for defining a relationship between the layers included in the machine learning model. According to an embodiment, the structure-generating apparatus 100 may load a machine learning model that has been updated using the model information database 123, to generate a structure candidate that has an inputted target physical property. The generated structure candidate is examined to check whether a predicted physical property matches a target physical property, whether an improper structure is detected, and whether it is a duplicate structure that is already stored in the material information database 122. Thereafter, information relating to the generated structure candidate (e.g., a character string indicating the structure) is stored in the material information database 122. In this case, the descriptor information of the material, the 3D structure information, and the like may be grouped and stored in the material information database 122.

The workflow illustrated in FIG. 2 is a circulating process in which a structure candidate of a new material is generated based on the machine learning model, and the quantum computation is performed on the structure candidate to continuously update the machine learning model. As a result, the structure-generating apparatus 100 according to an embodiment can evolve the machine learning model property into a physical property that is not stored in the material information database 122.

The machine learning model may be updated in a direction of searching for a target physical property by repeatedly performing the workflow illustrated in FIG. 2. According to an embodiment, as an operating condition of the structure-generating processor 110 is determined depending on a target physical property, a workflow for generating a structure of a material having the target physical property may be repeatedly performed, and the structure-generating apparatus 100 can continuously generate a structure of a new material that satisfies the target physical property.

Figure 3:
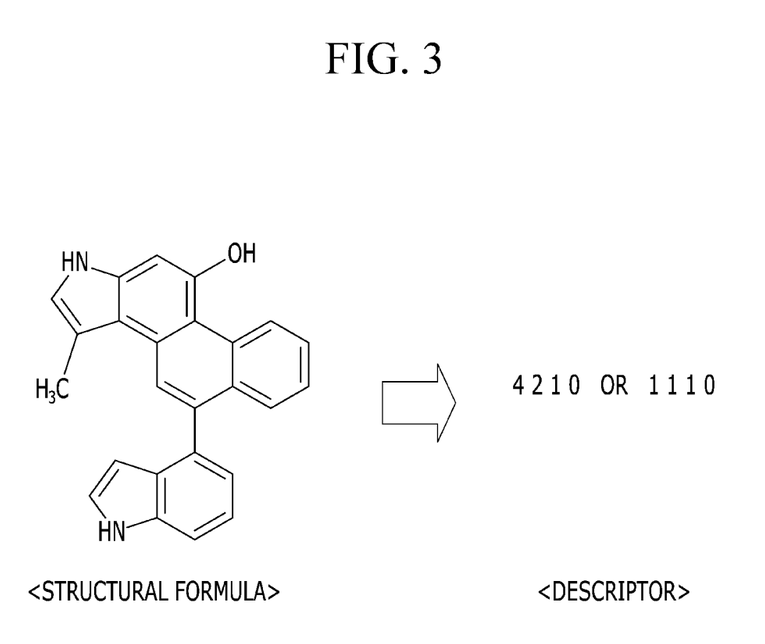
FIG. 3 is an exemplary embodiment of a structural formula of a material and a relationship to a descriptor of the material.

FIG. 3 illustrates an exemplary embodiment of a structural formula of a material and a relationship with a descriptor of the material.

The structure of the material (hereinafter referred to as 'the structure') indicates an atomic-level structure of the material. The structure is represented at the atomic level to derive a physical property using a first principle simulation to design a new material candidate. The structure may be represented as a structural formula based on a relationship (e.g., a chemical bond) between atoms or as a character string (e.g., one-dimensional). As a format of the character string representing the structure, a SMILES code, an InChI (International Chemical Identifier) code, or the like may be employed. For example, the character string indicating the structural formula of the structure may be represented as Equation 1.

$$OC1=C(C=C2C=CNC2=C1)C1=C(C=CC=C1)$$
$$C1=CC2=C(NC=C2)C=C1 \qquad \text{Equation 1}$$

The descriptor of the material (hereinafter referred to as 'the descriptor') indicates an index value used for representing a character of the material, and can be obtained by performing a calculation on a prepared material. The descriptor according to an embodiment may include a molecular structure fingerprint (e.g., a Morgan fingerprint or extended connectivity fingerprint (ECFP)) indicating whether a specific partial structure is included, or a quantitative structure-property relationship (QSPR) descriptor having an immediately calculable value such as the number of a partial structure (e.g., a ring) included in a molecular weight or a molecular structure. Table 1 shows the descriptors according to an embodiment.

TABLE 1

| Partial structure | Number |
|---|---|
|  | 4 |
|  | 2 |
|  | 1 |

TABLE 1-continued

| Partial structure | Number |
|---|---|
| (fluorene structure) | 0 |

Referring to FIG. 3 and Table 1, a descriptor "4210" may be determined based on the number of partial structures included in the structure of the material. When the descriptor is represented by using a binary code, the descriptor may be represented as "1110."

In this case, "1" or "0" indicates whether a partial structure is included. For example, 1 may indicate that the partial structure is included, and 0 may indicate that the partial structure is not included.

The physical property of the material (hereinafter referred to as 'the physical property') indicates an empirical or a calculated property of the material, which can be a value measured through experiment or calculated through simulations. For example, when the material is a display material, the physical property may include a light transmission wavelength, a light-emitting wavelength, and the like. When the material is a battery material, the physical property may include a voltage. In contrast to the descriptor, the value of a physical property can involve complex calculations and simulations and can require a significant amount of time to derive the physical property.

Non-limiting examples of the physical property include molecular weight, boiling point, melting point, appearance, texture, color, odor, density, solubility, polarity, electronegativity, absorption, brittleness, capacitance, ductility, elasticity, electrical charge, electrical conductivity, thermal conductivity, electrical impedance, electric potential, electric field, emission, fluidity, hardness, inductance, intrinsic impedance, luminance, luminescence, luster, malleability, magnetic field, magnetic flux, moment, opacity, permeability, permittivity, plasticity, vapor pressure, radiance, resistivity, reflectivity, refractive index, specific heat, viscosity, wave impedance, crystallinity, crosslinking, glass transition temperature, tensile strength, elastic modulus, and the like.

Hereinafter, operations of the structure-generating processor 110 and the database 120 will be described in detail with reference to FIG. 4 and FIG. 5.

Figure 4:
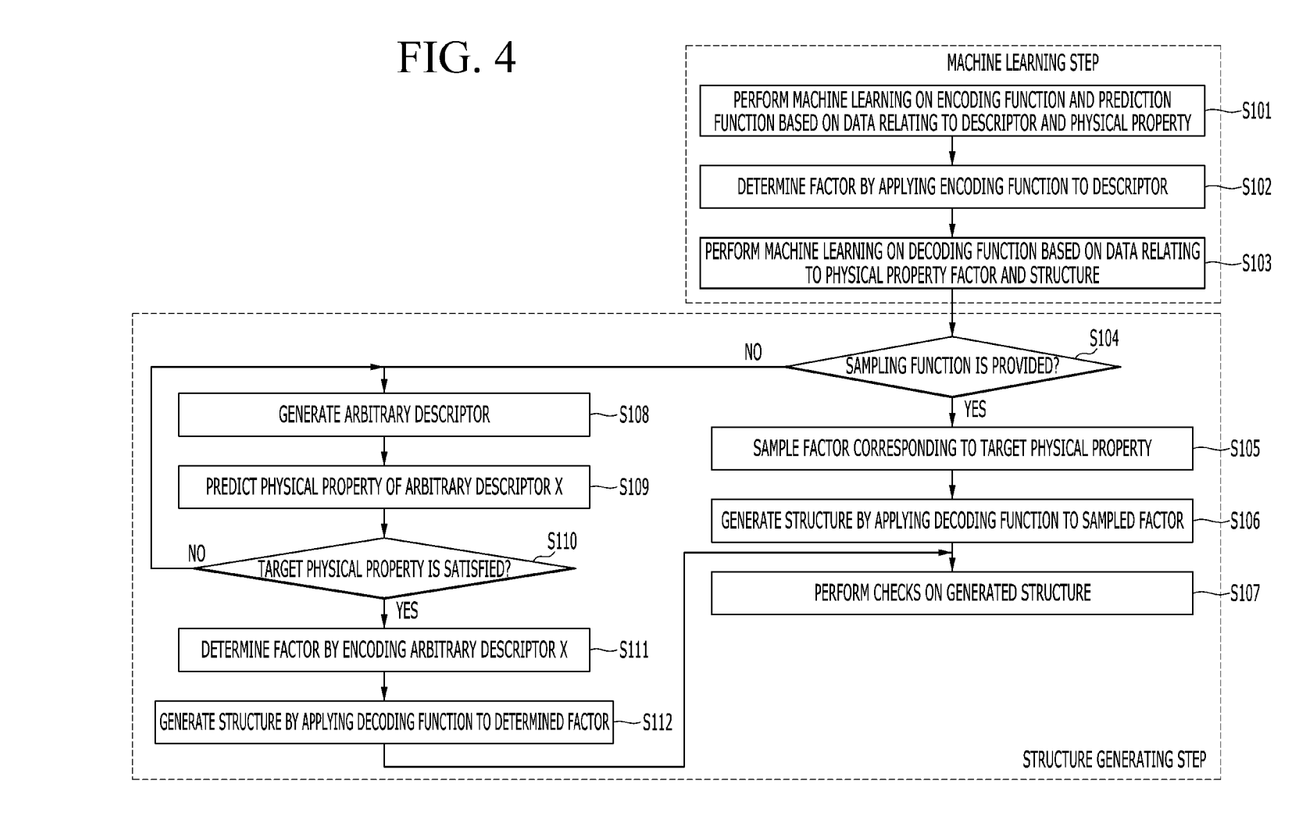
FIG. 4 is a flowchart illustrating an exemplary embodiment of a structure-generating method.

FIG. 4 is a flowchart illustrating an exemplary embodiment of a structure-generating method of a new material.

According to an embodiment, the structure-generating method of the new material includes a machine learning step and a structure-generating step. The structure-generating apparatus according to an embodiment determines a factor indicating a relationship between the descriptor, the physical property, and the structure, and determines a form of the machine learning model. In this case, the form of the machine learning model may be determined based on one or more parameter values used for the relationships between the descriptor, the physical property, the structure, and the factor.

The factor is an unrevealed key factor for representing a relationship between the descriptor data (x), the physical property data (y), and the structure data (s). The structure-generating processor 110 performs the machine learning based on a descriptor-physical property-structure relationship stored in the database 120 to determine the unrevealed key factor, and determines how the factor is connected with the descriptor, the physical property, and the structure. The factor may include a physical property factor related to a relationship between the descriptor and the physical property, and a structural factor related to a relationship between the physical property factor and the structure. Further, the factor may include a plurality of layers. When the physical property factor includes a plurality of layers, the structural factor indicating the relationship between the physical property factor and the structure may be determined for each layer.

First, the structure-generating processor 110 performs machine learning on an encoding function e(•) and a prediction function f(•) based on the descriptor-physical property relationship data (x, y) stored in the database 120 (S101). In other words, the structure-generating processor 110 learns the encoding function and the prediction function based on the descriptor-physical property relationship data (x, y). In this case, the structure-generating processor 110 can also learn a sampling function g(•). In an embodiment, the structure-generating processor 110 determines a factor (h=e(x)) by applying the learned encoding function e(•) to the descriptor data x (S102). The structure-generating processor 110 can determine a physical property factor to maximize the probability of the descriptor-physical property relationship data (x, y), or to minimize a difference between a physical property value f(e(x)) and the physical property data y.

Figure 5:
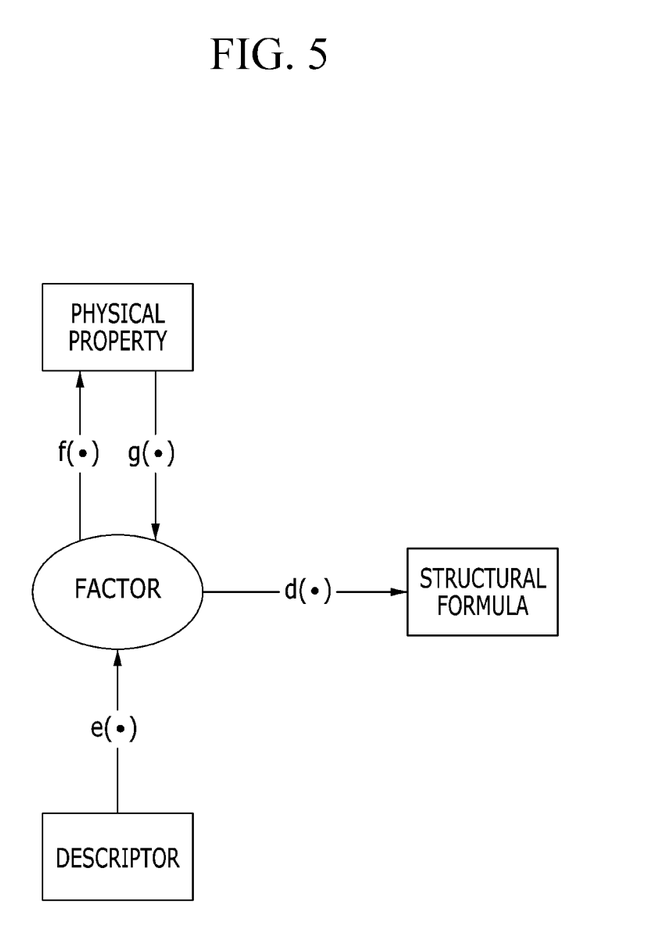
FIG. 5 is a schematic view illustrating an exemplary embodiment of a machine learning model.

FIG. 5 is a schematic view illustrating an exemplary embodiment of a machine learning model.

Referring to FIG. 5, the encoding function e(•) serves to derive the unrevealed key factor from the descriptor of the material. When the descriptor data x is used, the factor h(=e(x)) for the descriptor data x may be determined through the encoding function. The prediction function f(•) serves to predict the physical property of the material based on the factor obtained as an encoding result. When the physical property data y is used, y=f(h) is obtained by applying the prediction function to the factor h. The sampling function g(•) serves to derive a factor corresponding to the target physical property when the target physical property data y is given. When the factor h is derived by the sampling function, h=g(y) is obtained. According to an embodiment, since g(x) for a given target physical property may be generated in various forms instead of being determined to have one form, the structure-generating processor 110 configures the sampling function such that different results are randomly obtained every time that an examination for accuracy of a generated structure is repeatedly performed.

The structure-generating processor 110 performs the machine learning on a decoding function d(•) based on data s (e.g., a structural formula) related to a structure of a material stored in the database 120 and a factor h (S103). The structural factor may be determined while the decoding function is learned. The decoding function d(•) serves to generate the structure of the material at an atomic level by using a factor derived from the physical property or the descriptor. When the structure is represented as S, S=d(h) is obtained.

Next, the structure-generating processor 110 generates a structure of a new material that has the target physical property based on a machine learning result.

When the sampling function is provided (S104), the structure-generating processor 110 samples the factor h (h=g(y)) corresponding to the target physical property (S104). In this case, when the factor includes a plurality of layers, each of the factors may be sampled. Then, the structure-generating processor 110 generates a structure by applying the decoding function d(•) to the determined factor (S106). Next, a validity check and a redundancy check are performed on the generated structure S (S107). In this case, when the decoder generates a plurality of structures for the sampled factors, the validity check and the redundancy check may be performed on each structure S of the plurality of structures. When no sampling function is provided, the structure-generating processor 110 generates an arbitrary descriptor x' (S108). In this case, the arbitrary descriptor x' may be generated by using a random binary code according to a fingerprint method, or may be generated by a Boltzmann machine. The generic algorithm serves to generate a new material candidate by using hybridization and modification of the existing material candidate, and the hybridization and the modification processes are arbitrary, and thus they can be used for generating the arbitrary descriptor x'.

The structure-generating processor 110 predicts a physical property of the generated arbitrary descriptor x' (S109), and checks whether the predicted physical property y=f(e(x')) corresponds to the target physical property (S110). When the predicted physical property does not have the target physical property, the structure-generating processor 110 re-generates an arbitrary descriptor x' and predicts a physical property y=f(e(x')) thereof. When the predicted physical property has the target physical property, the structure-generating processor 110 determines a factor (h=e(x)) by encoding the descriptor data x (S111), and generates a structure S (S=d(h)) by applying the decoding function to the determined factor (S112). Next, the validity check and the redundancy check are performed on the generated structure S (S107).

Subsequently, if the generated structure S successively passes the validity check and the redundancy check, the generated structure S is determined as a structure candidate of the new material, and is added into the database 120. The structure candidate that is added into the database 120 may be subjected to an additional validity check through a simulation or the like.

Figure 6:
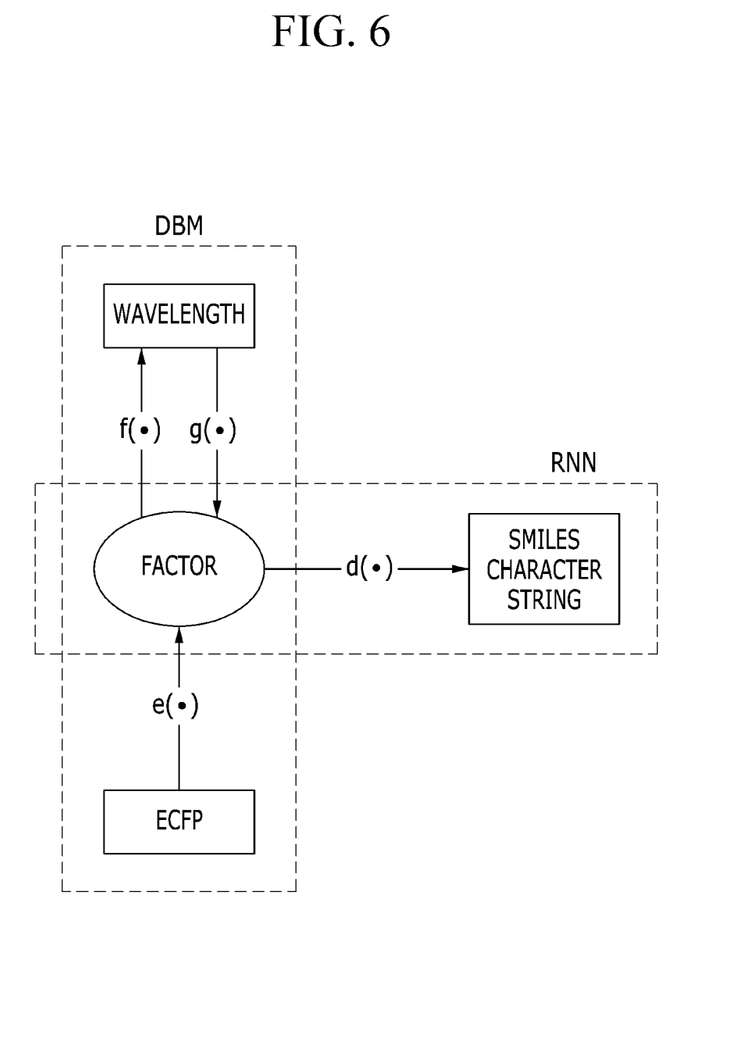
FIG. 6 is a schematic view illustrating an exemplary embodiment of a machine learning model.

FIG. 6 is a schematic view illustrating an exemplary embodiment of a machine learning model.

Referring to FIG. 6, an extended connectivity fingerprint (ECFP) is used as the descriptor, a light-emitting wavelength is used as the physical property, and a SMILES character string is used as the structure. According to another embodiment, the machine learning model includes a deep Boltzmann machine (DBM) portion that performs encoding, prediction, and sampling, and a recurrent neural network (RNN) that performs decoding.

In the DBM portion, the descriptor serves as a lowermost visual layer, the physical property serves as an uppermost target layer, and a plurality of hidden layers are disposed between the descriptor and the physical property. As the target layer, a Gaussian form of a layer indicating a real value or a softmax form of a layer indicating classification result may be used depending on a form of a physical property value. A unit value of each layer of the plurality of hidden layers may be a binary value. Then, one layer of the plurality of hidden layers may be designated to indicate a factor, in other words as a factor-indicating layer. For example, in the case of three hidden layers, an intermediate layer may be designated as the factor-indicating layer. The output (e.g., a generated structure S) of a decoder may be necessary to determine the factor-indicating layer from among the other layers of the plurality of hidden layers. For example, a layer in which the physical property of the generated structure is expected to have the target physical property may be determined as the factor-indicating layer.

According to another embodiment, the machine learning, the encoding, the prediction, and the sampling using a machine learning model in the DBM portion may be performed using any suitable techniques, for example known techniques. However, in the case of the encoding and prediction, the factor and the physical property may be calculated by inputting the descriptor and applying an inference algorithm to a remaining portion of the machine learning model. In the case of the sampling, the factor may be calculated by inputting the target physical property and applying a sampling algorithm.

The RNN portion may output a character string indicating the structure by using the factor determined in the DBM portion as an input of the machine learning model. The RNN portion may include two layers formed of long short-term memory (LSTM) units. A SMILES character string of a molecular structure code is used as the character string indicating the structure. The SMILES character string of molecular structure code may be grouped by three characters based on a start character, to be inputs and outputs in each time zone.

Figure 7:
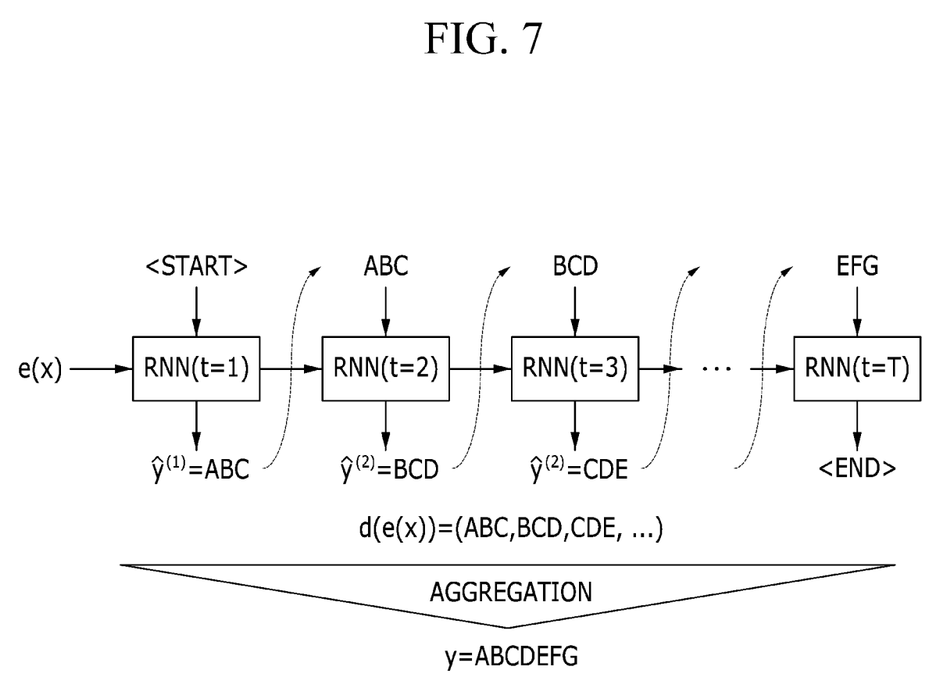
FIG. 7 is a schematic view illustrating an exemplary embodiment of a method of outputting a character string indicating a structure.

FIG. 7 is a schematic view illustrating an exemplary embodiment of a method of outputting a character string indicating a structure.

Referring to FIG. 7, when the structure S is represented as a character string of "ABCDEFG", the inputs and the outputs in each time zone may be "ABC", "BCD", "CDE", "DEF", and "EFG."

In other words, each unit of the RNN portion may use the next character of a character string that is inputted at a time t as an input at a time t+1.

The RNN portion may perform the machine learning to maximize a generation probability of the character string indicating the structure S for data (h, S) (i.e., factor and structure data). The generation probability p of the character string may be represented as Equation 2.

$$p(y \mid e(x)) = \prod_{t=1}^{T} p(y^{(t)} \mid e(x), y^{(1)}, \ldots , y^{(t-1)}) \quad \text{Equation 2}$$

When a configuration of the RNN portion is completed through the machine learning (i.e., when a parameter value of an RNN model used to determine the structural factor is determined), decoding may be performed on a factor obtained by decoding the descriptor or by sampling the physical property. According to another embodiment, the decoding is sequentially performed in a way in which a first portion S1 of the decoded character string S' is obtained by inputting the factor, a second portion S2 is obtained by inputting the obtained first portion S1, and a third portion is obtained by inputting the obtained second portion. Referring to FIG. 7, the first two characters of a character string S'(t) at a specific time point t are the same as last two characters of a character string S'(t−1) at a time point t−1. Next, the character strings S(t) at each time point are aggregated to output one character string S.

Figure 8:
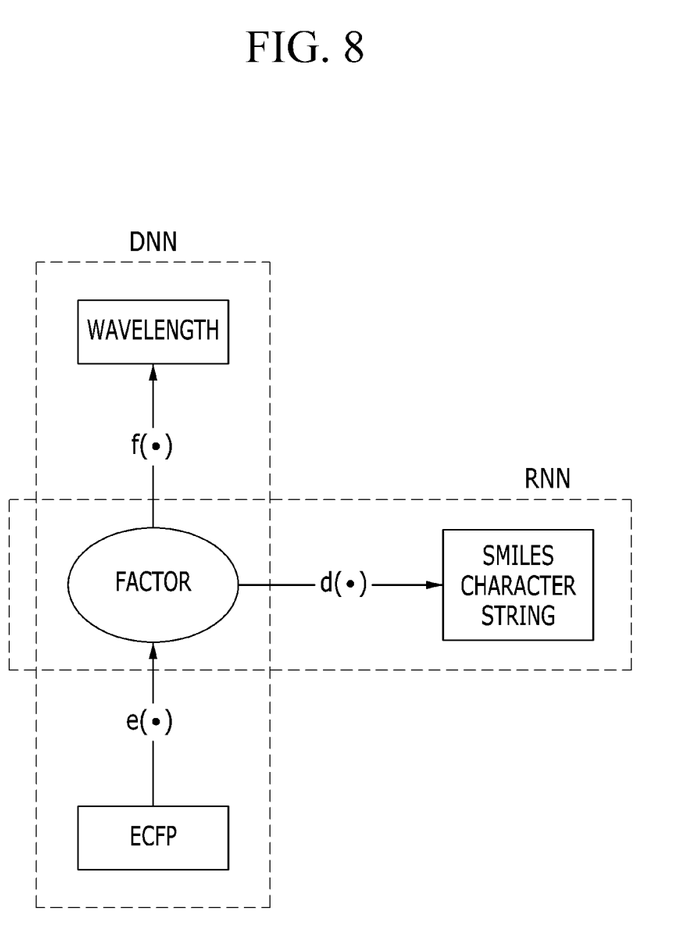
FIG. 8 is a schematic view illustrating an exemplary embodiment of a machine learning model.

FIG. 8 is a schematic view illustrating an exemplary embodiment of a machine learning model.

According to an embodiment, a deep neural network (DNN) may be used instead of the DBM. A SMILES character string may be generated by applying an encoding function learned by using a DNN model to the descriptor to obtain a factor, and by applying a decoding function learned by using the RNN model to the factor. When the machine learning step is performed by the DNN, a DNN portion has a descriptor as an input layer, a plurality of hidden layers indicating factors, and the physical property as an output layer. In the case of three hidden layers, a second layer (an intermediate layer) may be designated as a factor-indicating layer. The DNN model, which serves as a feed-forward type of neural network model, can precisely and quickly predict the physical property of an arbitrary descriptor. Accordingly, the DNN model may be used to design a structure candidate of a new material by predicting the physical properties of the many descriptors that are generated randomly. A generic algorithm may be used to randomly generate the many descriptors. In this case, the generic algorithm may be determined by maximizing a fitness function for comparing a predicted physical property of the descriptor with the target physical property.

Figure 9:
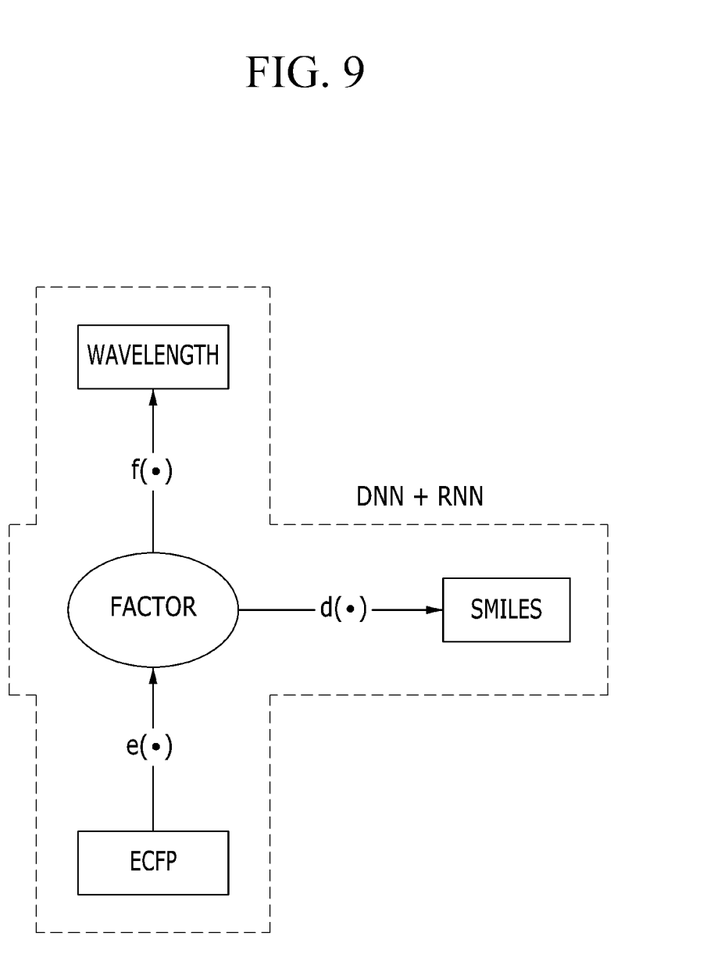
FIG. 9 is a schematic view illustrating an exemplary embodiment of a machine learning model.

FIG. 9 is a schematic view illustrating an exemplary embodiment of a machine learning model.

The aforementioned machine learning model has a two-step learning process in which a factor is derived from a relationship between the descriptor data x and the physical property data y, and a decoding function is learned from a relationship between the derived factor and the structure. In a first step of the two-step learning process, the structure-generating processor 110 determines f(•) and e(•) from the relationship y=f(e(x)). In a second step of the two-step learning process, the structure-generating processor 110 determines h=e(x) by using e(•) and determines d(•) from the relationship s=d(h). In this case, the e(•) that is determined based on the physical property data y in the first step is then used in the second step.

In a machine learning model according to another embodiment, the structure-generating processor 110 configures the two-step learning process as a single model to perform the machine learning as a single step. In this case, a factor that is advantageous in the structure generation can be derived by simultaneously using data related to the physical property and data related to the structure. Referring to FIG. 9, the structure-generating processor 110 determines f(•), d(•), and e(•) from a relationship [y, s]=[f(e(x)), d(e(x))]. Accordingly, in the machine learning model according to an embodiment, a difference between the d(e(x)) and the structure data s as well as a previously used difference f(e(x)) and the physical property data y are used to learn e(•).

For example, when |x| is an appropriate function indicating a magnitude, the first step and the second step of the two-step learning is represented as Equation 3.

First step: $\text{argmin}|\gamma - f(e(x))|$

Second step: $h=e(x) \rightarrow \text{argmin } |s-d(h)|$      Equation 3

In the second step of Equation 3, the form of e(•) is not changed, and is the same as in the first step.

However, in the machine learning which is performed as a single step, the relationship is represented as Equation 4.

$\text{argmin } \{|y-f(e(x))|+|s-d(e(x))|\}$

Figure 10:
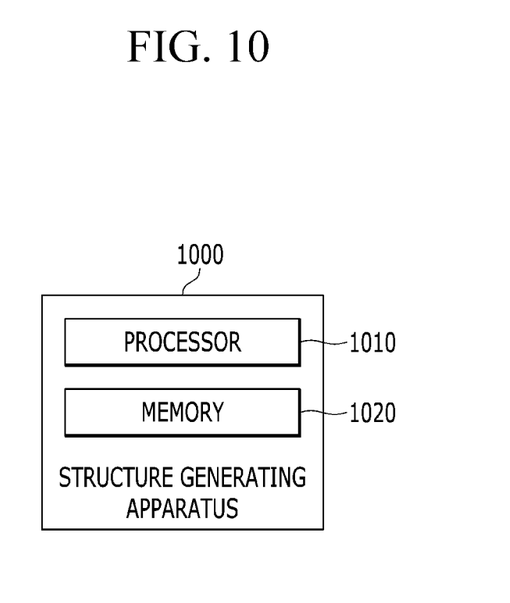
FIG. 10 is a block diagram illustrating an exemplary embodiment of a structure-generating apparatus.

FIG. 10 is a block diagram illustrating an exemplary embodiment of a structure-generating apparatus of a new material.

Referring to FIG. 10, the structure-generating apparatus 1000 according to an embodiment includes a processor 1010 and a memory 1020. The memory 1020 may be connected to the processor 1010 to store data for operating the processor 1010, or at least one program that is executed by the processor 1010. The processor 1010 may be configured to implement a function, a process, or a method that is suggested in an embodiment. An operation of the structure-generating apparatus 1000 according to an embodiment may be implemented by the processor 1010.

In an embodiment, the memory 1020 may be disposed at an interior or exterior of the processor, and may be connected to the processor by any suitable means, including already-known means. The memory 1020 may be selected from volatile and non-volatile storing media. For example, the memory may include a read-only memory (ROM), a random access memory (RAM), or a combination thereof.

While this invention has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

What is claimed is:

1. A structure-generating method for generating a structure candidate of a new material, the method comprising:
   by a structure-generating processor:
   determining a factor about relationships among a descriptor of a material, a physical property of the material, and a structure of the material by performing machine learning on a machine learning model, wherein the machine learning model is configured to provide a result including the factor based on the descriptor of the material, the physical property of the material and the structure of the material; and
   generating a structure candidate of the new material based on the result including the factor from the machine learning, wherein the new material has a target physical property, and wherein the descriptor of the material, the physical property of the material, and the structure of the material are stored in a database.

2. The structure-generating method of claim 1, wherein the performing the machine learning on the machine learning model configured to provide a result including the factor based on the descriptor of the material, the physical property of the material, and the structure of the material comprises:
   by the structure-generating processor:
   determining the factor indicating a relationship between the descriptor and the physical property by performing the machine learning on a relationship between the descriptor and the physical property; and
   performing the machine learning on a relationship between the factor and the structure; and
   generating the structure of the material based on a result of the machine learning on the relationship between the factor and the structure.

3. The structure-generating method of claim 2, wherein the performing the machine learning on the relationship between the factor and the structure comprises:
   by the structure-generating processor:
   determining a structural factor indicating the relationship between the factor and the structure.

4. The structure-generating method of claim 3, wherein the factor comprises a plurality of layers, and
   the determining of the structural factor comprises:
   by the structure-generating processor:
   determining the structural factor for each layer of the plurality of layers.

5. The structure-generating method of claim 2, wherein the determining of the factor comprises:

by the structure-generating processor:
  learning an encoding function for deriving the factor from the descriptor based on data related to each of the descriptor and the physical property; and
  determining the factor by applying the encoding function to the descriptor.

6. The structure-generating method of claim 2, wherein the performing the machine learning on the relationship between the factor and the structure further comprises:
  by the structure-generating processor:
  learning a decoding function for generating the structure candidate from the factor based on data relating to each of the factor and the structure.

7. The structure-generating method of claim 6, wherein the generating the structure candidate comprises:
  by the structure-generating processor:
  sampling a factor corresponding to the target physical property; and
  generating the structure candidate by applying the decoding function to the factor corresponding to the target physical property.

8. The structure-generating method of claim 2, wherein the performing the machine learning on the machine learning model configured to provide a result based on the descriptor of the material, the physical property of the material, and the structure of the material further comprises:
  by the structure-generating processor:
  learning a prediction function for predicting the physical property from the factor based on data relating to each of the descriptor and the physical property.

9. The structure-generating method of claim 8, wherein the generating the structure candidate further comprises:
  by the structure-generating processor:
  generating an arbitrary descriptor;
  predicting a physical property of a material corresponding to the arbitrary descriptor by applying the prediction function to the arbitrary descriptor; and
  determining whether the predicted physical property of the material corresponding to the arbitrary descriptor has the target physical property.

10. The structure-generating method of claim 9, wherein the generating of the structure candidate further comprises:
  by the structure-generating processor:
  when the predicted physical property of the material corresponding to the arbitrary descriptor does not have the target physical property:
  generating an arbitrary descriptor different from the arbitrary descriptor;
  predicting a physical property of a material corresponding to the different arbitrary descriptor by applying the prediction function to the different arbitrary descriptor; and
  determining whether the predicted physical property of the material corresponding to the different arbitrary descriptor has the target physical property.

11. The structure-generating method of claim 9, wherein the generating of the structure candidate further comprises:
  by the structure-generating processor:
  when the predicted physical property of the material corresponding to the arbitrary descriptor has the target physical property:
  determining a factor corresponding to the arbitrary descriptor by applying an encoding function for deriving the factor corresponding to the arbitrary descriptor; and
  generating a structure candidate corresponding to the arbitrary descriptor by applying a decoding function for generating the structure candidate from the factor corresponding to the arbitrary descriptor.

12. The structure-generating method of claim 11, further comprising:
  by the structure-generating processor:
  performing a validity check and a redundancy check on the structure candidate corresponding to the arbitrary descriptor.

13. A structure-generating apparatus for generating a structure candidate of a new material, the apparatus comprising:
  a database configured to store a descriptor of a material, a physical property of the material, and a structure of the material; and
  a structure-generating processor configured to:
  determine a factor about relationships among a descriptor of a material, a physical property of the material, and a structure of the material by performing machine learning on a machine learning model, wherein the machine learning model is configured to provide a result based on the descriptor of the material, the physical property of the material, and the structure of the material, and
  generate a structure candidate of the new material based on the result including the factor from the machine learning, wherein the new material has a target physical property.

14. The structure-generating apparatus of claim 13, wherein, when performing the machine learning on the machine learning model configured to provide a result including the factor based on the descriptor of the material, the physical property of the material, and the structure of the material,
  the structure-generating processor is configured to:
  determine the factor indicating a relationship between the descriptor and the physical property by performing the machine learning on a relationship between the descriptor and the physical property, and
  perform the machine learning on a relationship between the factor and the structure to generate the structure of the material based on the factor.

15. The structure-generating apparatus of claim 14, wherein, when performing the machine learning on the relationship between the factor and the structure,
  the structure-generating processor is further configured to determine a structural factor indicating the relationship between the factor and the structure.

16. The structure-generating apparatus of claim 15, wherein the factor comprises a plurality of layers, and,
  when determining the structural factor,
  the structure-generating processor is further configured to determine the structural factor for each layer of the plurality of layers.

17. The structure generating apparatus of claim 14, wherein when determining the factor,
  the structure-generating processor is further configured to learn an encoding function for deriving the factor from the descriptor based on data related to each of the descriptor and the physical property, and to determine the factor by applying the encoding function to the descriptor.

18. The structure-generating apparatus of claim 14, wherein, when performing the machine learning on the relationship between the factor and the structure, the structure-generating processor is further configured to learn a decoding function for generating the structure candidate from the factor based on data relating to each of the factor and the structure.

19. The structure-generating apparatus of claim 18, wherein, when generating the structure candidate,
the structure-generating processor is further configured to:
samples a factor corresponding to the target physical property, and
generate the structure candidate by applying the decoding function to the factor corresponding to the target physical property.

20. The structure-generating apparatus of claim 14, wherein, when performing the machine learning on the machine learning model configured to provide a result based on the descriptor of the material, the physical property of the material, and the structure of the material,
the structure-generating processor is further configured to learn a prediction function for predicting the physical property from the factor based on data relating to each of the descriptor and the physical property.

21. The structure-generating apparatus of claim 20, wherein, when generating the structure candidate,
the structure-generating processor is further configured to:
generate an arbitrary descriptor,
predict a physical property of a material corresponding to the arbitrary descriptor by applying the prediction function to the arbitrary descriptor, and
determine whether the predicted physical property of the material corresponding to the arbitrary descriptor has the target physical property.

22. The structure-generating apparatus of claim 21, wherein, when generating the structure candidate,
when the predicted physical property of the material corresponding to the arbitrary descriptor does not have the target physical property:
the structure-generating processor is further configured to:
generate an arbitrary descriptor different from the arbitrary descriptor,
predict a physical property of a material corresponding to the different arbitrary descriptor by applying the prediction function to the different arbitrary descriptor, and
determine whether the predicted physical property of the material corresponding to the different arbitrary descriptor has the target physical property.

23. The structure-generating apparatus of claim 21, wherein, when generating the structure candidate,
when the predicted physical property of the material corresponding to the arbitrary descriptor has the target physical property:
the structure-generating processor is further configured to:
determine a factor corresponding to the arbitrary descriptor by applying an encoding function for deriving the factor to the arbitrary descriptor, and
generate a structure candidate corresponding to the arbitrary descriptor by applying a decoding function for generating the structure candidate from the factor corresponding to the arbitrary descriptor.

24. The structure-generating apparatus of claim 23, wherein the structure-generating processor is further configured to perform a validity check and a redundancy check on the structure candidate corresponding to the arbitrary descriptor.

* * * * *